US010596031B2

(12) United States Patent
Yetik

(10) Patent No.: US 10,596,031 B2
(45) Date of Patent: Mar. 24, 2020

(54) MACULAR HOLE REPAIRMENT INSTRUMENT

(71) Applicant: Hüseyin Yetik, Istanbul (TR)

(72) Inventor: Hüseyin Yetik, Istanbul (TR)

( * ) Notice: Subject to any disclaimer, the term of this patent is extended or adjusted under 35 U.S.C. 154(b) by 173 days.

(21) Appl. No.: 15/306,082

(22) PCT Filed: Apr. 21, 2015

(86) PCT No.: PCT/TR2015/000163
§ 371 (c)(1),
(2) Date: Oct. 21, 2016

(87) PCT Pub. No.: WO2015/171087
PCT Pub. Date: Nov. 12, 2015

(65) Prior Publication Data
US 2017/0042729 A1    Feb. 16, 2017

(30) Foreign Application Priority Data

May 7, 2014    (TR) .................................. 2014/05127

(51) Int. Cl.
*A61F 9/007*    (2006.01)
(52) U.S. Cl.
CPC .............................. *A61F 9/00727* (2013.01)
(58) Field of Classification Search
CPC .................................................. A61F 9/00727
USPC .................................................. 606/205, 207
See application file for complete search history.

(56) References Cited

U.S. PATENT DOCUMENTS

| | | | | | |
|---|---|---|---|---|---|
| 3,964,468 | A | * | 6/1976 | Schulz .................. | A61B 10/06 600/564 |
| 4,950,273 | A | * | 8/1990 | Briggs ............... | A61B 17/2833 30/251 |
| 4,982,727 | A | * | 1/1991 | Sato ....................... | A61B 17/29 600/104 |
| 5,052,402 | A | * | 10/1991 | Bencini .................. | A61B 10/06 600/564 |
| 5,094,247 | A | * | 3/1992 | Hernandez ............. | A61B 10/06 600/564 |
| 5,147,369 | A | * | 9/1992 | Wagner .................. | A61B 17/30 294/99.2 |
| 5,209,747 | A | * | 5/1993 | Knoepfler ............. | A61B 17/29 604/22 |
| 5,405,344 | A | * | 4/1995 | Williamson ....... | A61B 17/1285 606/1 |

(Continued)

FOREIGN PATENT DOCUMENTS

| | | |
|---|---|---|
| DE | 102011100371 A1 | 11/2012 |
| WO | 0076403 A1 | 12/2000 |
| WO | 0168016 A2 | 9/2001 |

OTHER PUBLICATIONS

International Search Report of PCT/TR2015/000163, dated Sep. 25, 2015.

*Primary Examiner* — Julian W Woo
(74) *Attorney, Agent, or Firm* — Marshall, Gerstein & Borun LLP

(57) ABSTRACT

The invention relates to an instrument which has been developed to be used in macular hole surgeries closes and repairs the macular hole by drawing the retina, wherein it comprises a holder comprising at least one shaft connected to the handle, and at least one pressure leg positioned to the end of the shaft.

4 Claims, 4 Drawing Sheets

(56) References Cited

U.S. PATENT DOCUMENTS

| | | | | |
|---|---|---|---|---|
| 5,423,855 | A * | 6/1995 | Marienne | A61B 17/2833 |
| | | | | 606/206 |
| 5,520,678 | A * | 5/1996 | Heckele | A61B 17/29 |
| | | | | 606/1 |
| 5,693,069 | A * | 12/1997 | Shallman | A61B 17/22031 |
| | | | | 606/110 |
| 6,827,086 | B2 * | 12/2004 | Shuman | A61B 17/12 |
| | | | | 128/898 |
| 6,860,179 | B2 * | 3/2005 | Hopper | B25B 5/06 |
| | | | | 81/318 |
| 8,105,350 | B2 * | 1/2012 | Lee | A61B 1/00071 |
| | | | | 606/205 |
| 8,801,752 | B2 * | 8/2014 | Fortier | A61B 17/29 |
| | | | | 606/205 |
| 8,968,355 | B2 * | 3/2015 | Malkowski | A61B 17/29 |
| | | | | 606/205 |
| 9,005,238 | B2 * | 4/2015 | DeSantis | A61B 1/008 |
| | | | | 606/205 |
| 9,039,737 | B2 * | 5/2015 | Vold | A61F 9/007 |
| | | | | 606/219 |
| 9,962,255 | B1 * | 5/2018 | Weiss | A61F 2/14 |
| 2008/0147083 | A1 * | 6/2008 | Vold | A61B 17/0644 |
| | | | | 606/107 |
| 2015/0018806 | A1 * | 1/2015 | Olsen | A61F 9/00727 |
| | | | | 606/4 |

* cited by examiner

MACULAR HOLE REPAIRMENT INSTRUMENT

TECHNICAL FIELD

The invention relates to an instrument which has been developed to be used in macular hole surgeries, closes and repairs the macular hole by drawing the retina tissue toward the center in the macula.

STATE OF THE ART

Macula is the name of the retina area which is used when looking at a point in the target, namely, provides central vision. It is also referred to as the "area of the central vision". In this area, holes which looks like as if being bored using a puncher may be formed. This is called macular hole. Surgical operation is the only treatment method.

The existing macular hole repair operations comprise the processes of vitrectomy, namely removing the vitreous gel tissue filling inside of the eye, peeling the internal limiting membrane (ILM), the layer covering surface area of the macula as well as whole retina, and applying gas (air) tamponade.

However, the desired surgical success cannot always be achieved subsequent to performing these processes. During operation, closing the macular hole mechanically by drawing the same from the periphery toward the center increases the surgical success rate up to around 100%. When retina, a soft, dough-like tissue, is drawn from the edge of the hole toward the center of the same by a soft push, it is closed in the same manner as in the case of closing the hole section of a play dough the center of which is punched. Said surgical technique has also been developed by the present inventor.

After the standard surgical steps mentioned above, the fact that the present macular hole is closed 360 degrees toward the center by means of mechanical drawing method in a sensitive manner before applying the gas (air) tamponade, increases the success rate with respect to closing the hole up to around 100%.

However, a sensitive instrument which draws and closes macular hole having a diameter around 500 microns, mechanically with this sensitivity is not available. Thus, this process is achieved by using other vitreoretinal surgical instruments such as round blunt side of the forceps used for peeling the internal limiting membrane (ILM) or flute needle, etc. However, having not been designed for a sensitive process as such, these instruments can damage the sensitive macula and retina pigment epithelium.

To conclude, due to the aforementioned drawbacks and the inadequacy of the existing solutions regarding the subject, a development is deemed to be necessary in the related technical field.

OBJECT OF THE INVENTION

The invention aims to develop a new surgical instrument and to eliminate the drawbacks resulting in surgical failure in the operations for macular hole closure.

The object of the invention is to increase the success rate with respect to macular hole closure up to 100%.

One object of the invention is to shorten the duration of macular hole closure operation and to provide convenience for the surgeon during operation.

One object of the invention is to present a sensitive instrument which draws and closes macular hole mechanically and sensitively.

Another object of the invention is to achieve a surgical treatment without damaging the macula and retina pigment epithelium.

In order to achieve the objects mentioned above, the invention is a macular hole instrument which is used for mechanical macular hole closure in the macular hole surgeries and comprises a handle, wherein it also comprises a holder comprising at least one shaft connected to the handle, and at least one pressure leg positioned to the end of the shaft. Said holder is connected to the handle from a connection point. Said holder comprises two shafts and a total of two pressure applying and holding (serving as forceps) legs each of which will be positioned to the end of each shaft.

In a preferred embodiment of the invention, said pressure legs comprise inner sections and are positioned such that the inner sections thereof will face each other and form a sphere when coming together.

In a preferred embodiment of the Invention, said shafts with pressure legs being positioned to the ends thereof are positioned in a manner to be combined in the central axis extension of said handle.

In a preferred embodiment of the invention, said connection point comprises a moveable connection which allows the holder to move independent of the handle.

In a preferred embodiment of the Invention, said pressure legs comprise a moveable connection which allows independent movement thereof from said shaft.

In a preferred embodiment of the invention, said pressure legs have a hemisphere shape.

The structural and characteristic features and all the advantages of the present invention will be more clearly understood thanks to the figures below and the detailed description written with reference to those figures and therefore, the evaluation needs to be done by taking said figures and the detailed description into consideration.

FIGURES FACILITATING UNDERSTANDING OF THE INVENTION

DESCRIPTION OF THE REFERENCES

Figure 1:
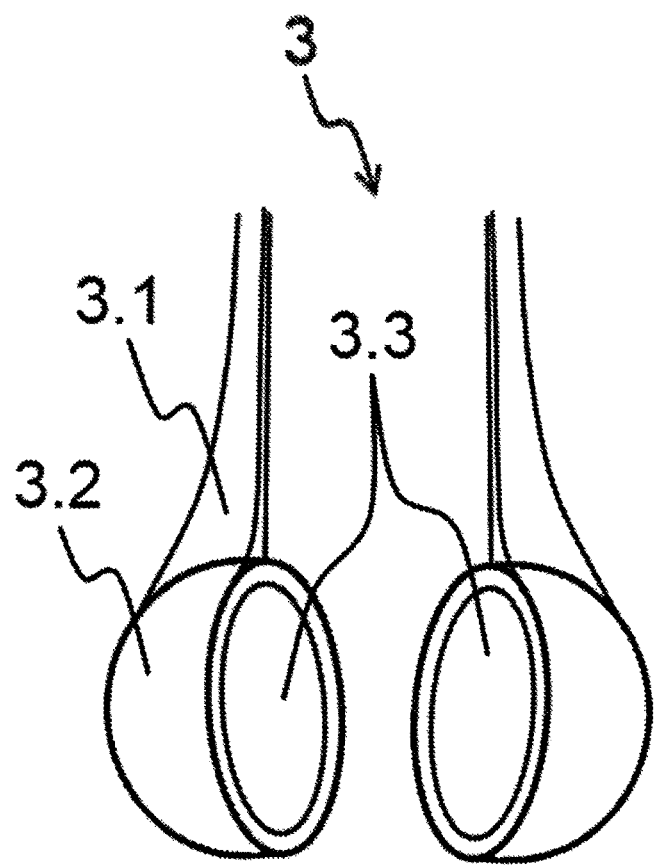
FIG. 1 is the view of the forceps pressure legs (holders) of the instrument according to the invention.
Figure 2:
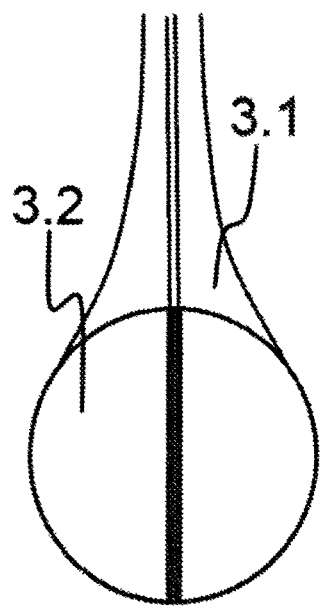
FIG. 2 is the view of the spherical structure obtained when the inner sections of the forceps pressure legs of the instrument according to the invention are closed in a manner to face each other.
Figure 3:
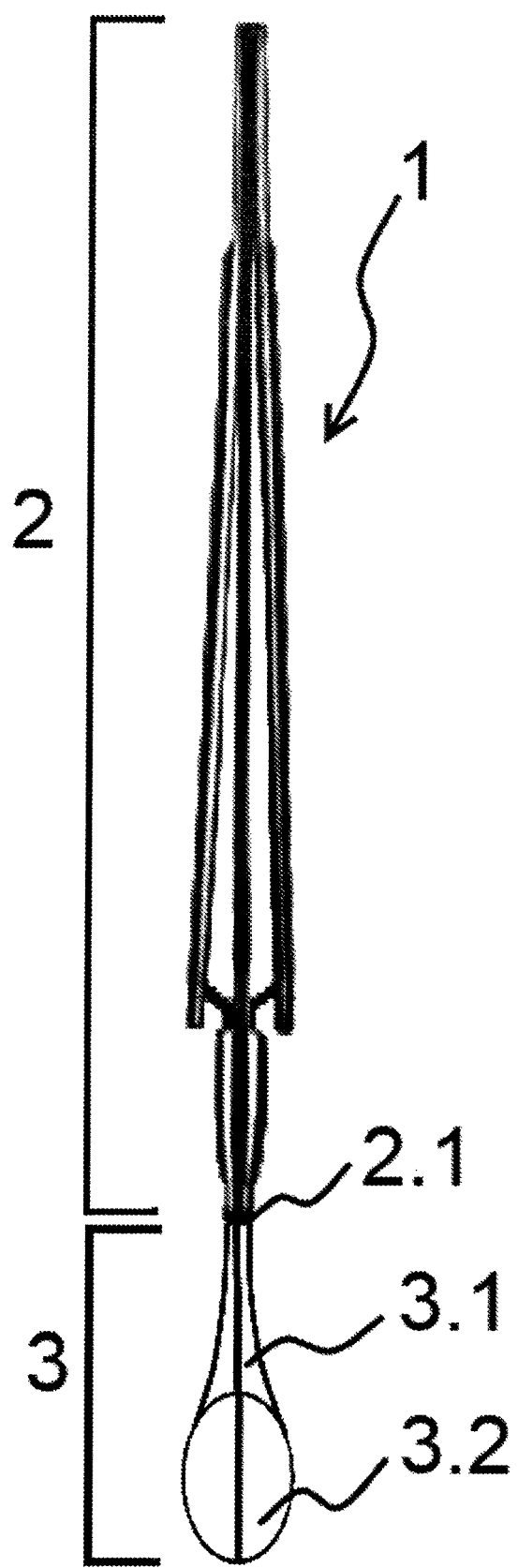
FIG. 3 is the spherical view obtained when the inner sections of the forceps pressure legs of the instrument according to the invention are closed in a manner to face each other.
Figure 4:
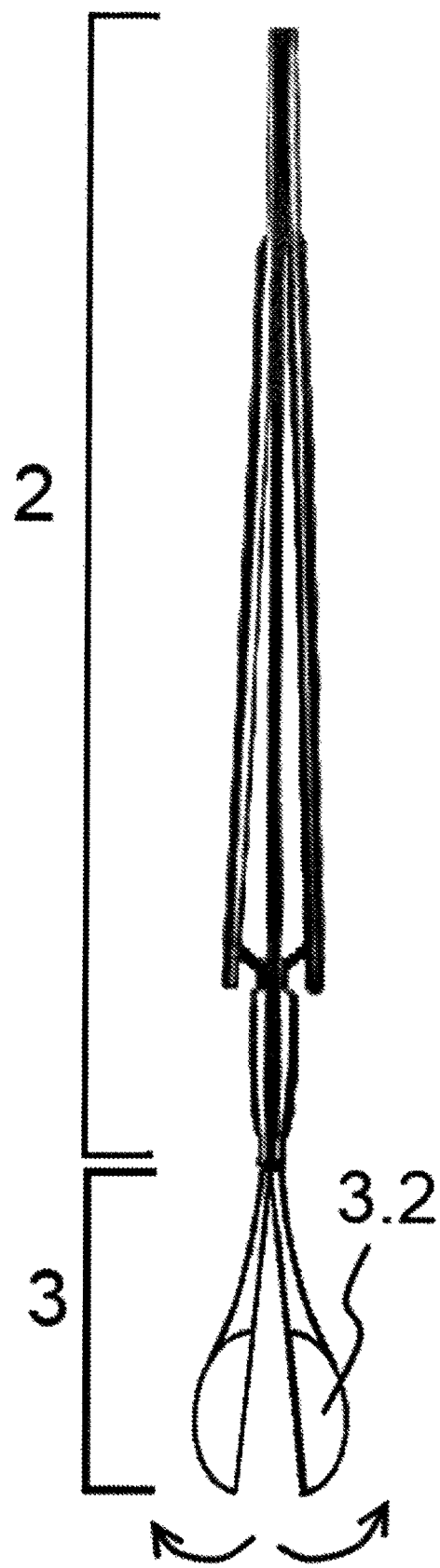
FIG. 4 is the view of the end section of the instrument, namely the forceps pressure legs according to the invention, when opened.

1. Macular Hole Repairment Instrument
2. Handle
2.1. Connection point
3. Holder
3.1. Shaft
3.2. Pressure Legs
3.2.1 Pressure Surfaces
3.3 Inner Section The drawings do not need to be scaled and the details that are not necessary for understanding the present invention may have been ignored. Besides, the members that are at least substantially identical or have at least substantially identical functions are referred with the same number.

DETAILED DESCRIPTION OF THE INVENTION

In this detailed description, the preferred embodiments of the instrument according to the invention used in the macular hole treatment are described only for a better understanding of the subject.

In general terms, macular hole closure instrument (1) according to the invention consists of a handle (2) which is also available in standard forceps, holder (3) and connection point (2.1) where the holder (3) is connected to the handle (2). The connection point (2.1) can comprise a hinge-like connection member as well as serving as a continuing part of the handle (2) by means of welding. Said holder (3) comprises shaft (3.1) and pressure legs (3.2) comprising inner sections (3.3).

The handle (2) is a standard structure which is also available in all other instruments used in vitreoretinal surgeries and comprises a collapsible mechanism with spring.

The pressure legs (3.2) have a hemisphere shape preferably. Therefore, inner sections (3.3) of said pressure legs (3) have also a hemispherical inner volume. In an alternative embodiment, they can be designed in various shapes or forms.

When the holder (3) is used in a closed state, namely when the pressure legs (3.2) are combined such that the inner sections (3.3) thereof will face each other, a shape of sphere is obtained. In this manner, macular hole closure instrument (1) according to the invention having a spherical end allows the macular hole to be drawn and closed mechanically (without damaging or with a minimum damage to the macula and pigment epithelium).

The instrument according to the invention, in addition to allowing mechanical closure of the macular hole, functions as forceps to be used for peeling ILM or removing the residues of ILM or glial tissue appearing during the closure of the macular hole by mechanical drawing.

Usage of the Invention;

Standard macular hole surgical process is achieved by including also peeling the ILM. The macular hole closure instrument (1) according to the invention is entered into the eye with the holder (3) being closed. The instrument is drawn from the periphery toward the center by a spherical end, thereby allowing the mechanical closure of the macular hole. Subsequent to drawing, residues of the surface glial tissue drawn toward the center of the macular hole are removed by the holder (3) when opened and used as forceps this time.

Peeling ILM is also achieved with the invention. In other words, the instrument can also be used as ILM forceps. As the edges thereof are designed to be thin, it is also used to serve as ILM forceps.

Figures 5, 6, 7:
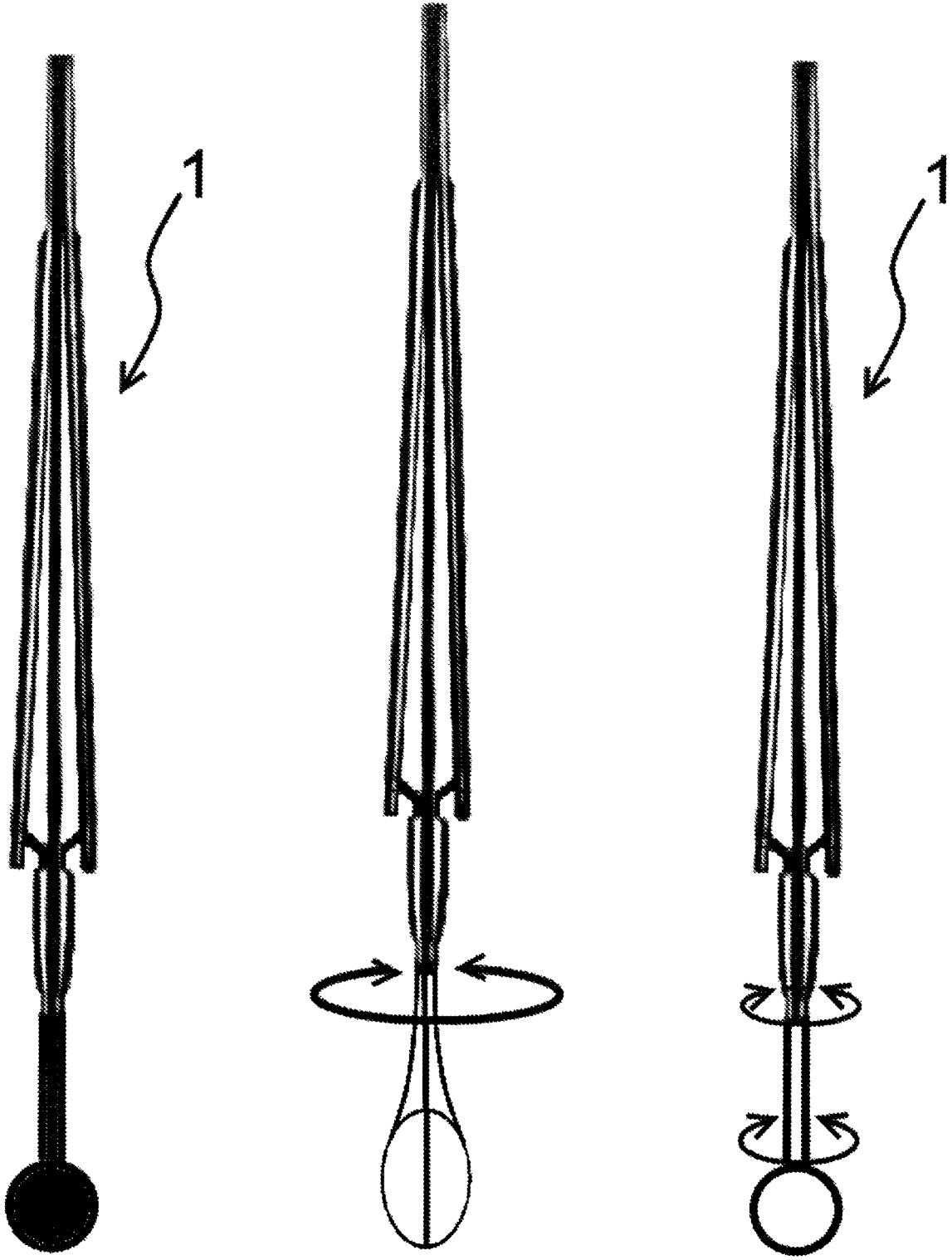
FIG. 5 is the view of the instrument according to the invention with a holder comprising a single spherical pressure leg.
FIG. 6 is the illustration of the connection point-centered movement of the holder of the instrument according to the invention.
FIG. 7 is the illustration of the movement from section where pressure leg of the instrument according to the invention is connected with the shaft of the same.

In the alternative embodiments of the instrument, the holder (3) can be provided to be one-piece, namely not to be a collapsible structure. As a continuing part of the handle (2), it can comprise a single shaft (3.1) and a spherical pressure leg (3.2) at the end section of this shaft (3.1) (FIG. 5).

In another alternative embodiment, the connection point (2.1) can have the characteristics of a joint or ball connection member. The holder (3) can move to various directions by centering on the connection point (2.1) (FIG. 6). Besides, connection of the pressure leg (3.2) with the shaft (3.1) can also be a moveable connection (e.g. hinge-like) (FIG. 7).

In another alternative embodiment, the holder (3) can be fitted into the handle (2) along the shaft (3.1).

Some combinations of said alternative embodiments can be presented together.

Figure 8:
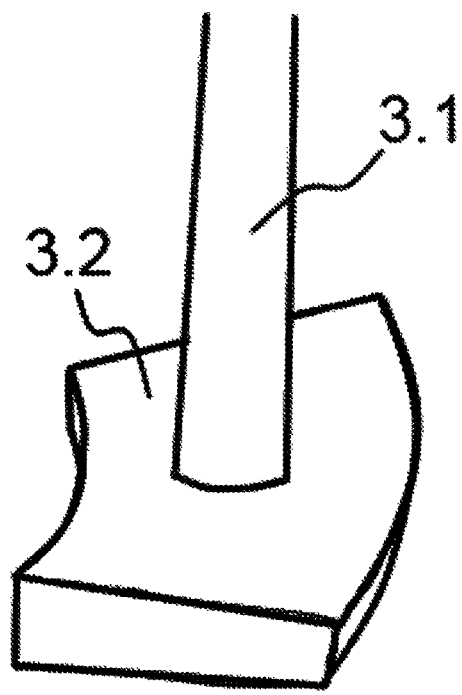
FIG. 8 and FIG. 9 are the illustrations of the alternative forms of the instrument with a single pressure leg according to the invention.
Figure 8A:
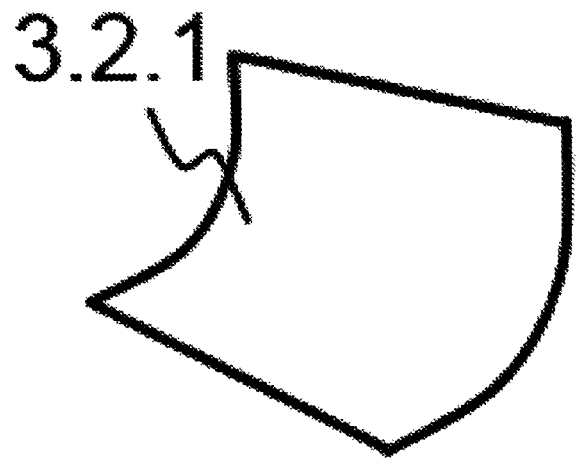
FIG. 8a and FIG. 9a are the illustrations of the various forms of pressure surfaces of the instrument with a single pressure leg according to the invention.
Figure 9:
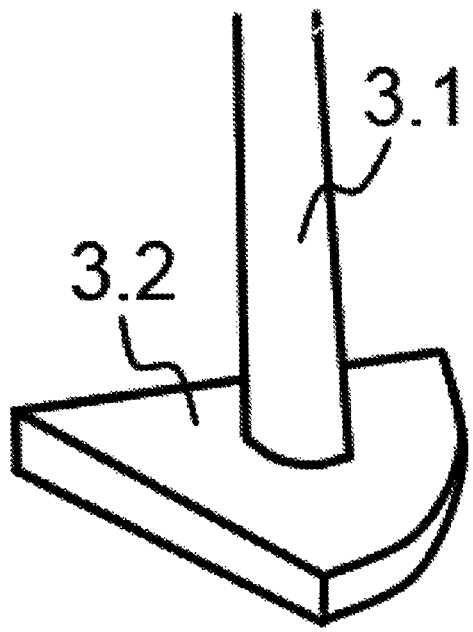
Figure 9A:
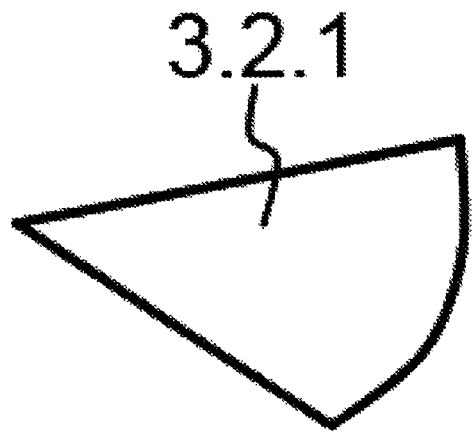

In the embodiment according to the invention, rather than the spherical end section, the bottom surface contacting the retina, namely the pressure surface (3.2.1) of the retina is important. When the pressure surface (3.2.1) is completely spherical sometimes, it can be incapable of removing by drawing the thin surface irregularities from the front thereof. Therefore, the bottom section (pressure surface (3.2.1)) of the pressure legs (3.2) contacting the retina can be formed to be quadrilateral (FIG. 8), with one edge being concave, the other edge being convex and the two side edges being flat. In addition, the pressure surface (3.2.1) can also be formed to be triangular, with two edges being flat and one edge being convex.

What is claimed is:

1. A macular hole repairment instrument for mechanical closure of macular hole in the macular hole surgeries, the instrument comprising:
    a handle; and a holder;
    the holder being connected to the handle through a connection point,
    wherein the connection point comprises a moveable connection, the moveable connection being a ball connection, which allows the holder to move independent of the handle;
    the ball connection allows the holder to move to various directions by centering on the connection point;
    the holder comprising at least one shaft connected to the handle;
    at least one pressure leg comprising a pressure surface positioned at the end of the shaft,
    wherein the pressure surface of the pressure legs configured to contact the retina is formed to be a quadrilateral shape, with two edges being flat, one edge being concave and the other edge being convex; or a triangular shape, with two edges being flat and one edge being convex to enable thin surface irregularities to be removed.

2. The instrument according to claim 1, wherein said holder comprises two shafts and a total of two pressure legs each of which is positioned to the end of each shaft.

3. The instrument according to claim 1, wherein said shafts with pressure legs being positioned to the ends thereof are positioned in a manner to be combined in the central axis extension of said handle.

4. The instrument according to claim 1, wherein said pressure legs comprise a moveable connection which allows independent movement thereof from said shaft.

* * * * *